United States Patent [19]
Hempel et al.

[11] Patent Number: 4,898,693
[45] Date of Patent: Feb. 6, 1990

[54] PROCESS FOR PRODUCTION OF 6α,9α-DIFLUORO-11β,17α-DIHYDROXY-16α-METHYL-4-PREGNENE-3,20-DIONE AND ITS DERIVATIVES

[75] Inventors: Gerhard Hempel, Werne; Mario Kennecke, Berlin; Bernhard Krieger, Unna; Rainer Phillippson, Bergkamen-Mitte; Hermann Triem, Hamm; Alfred Weber, Berlin, all of Fed. Rep. of Germany

[73] Assignee: Schering Aktiengesellschaft, Berlin and Bergkamen, Fed. Rep. of Germany

[21] Appl. No.: 126,098

[22] Filed: Nov. 30, 1987

[30] Foreign Application Priority Data

Nov. 28, 1986 [DE] Fed. Rep. of Germany ....... 3640709

[51] Int. Cl.4 .................................. C07J 9/00
[52] U.S. Cl. ................... 260/397.4; 260/377.2
[58] Field of Search .................... 260/397.2, 397.4

[56] References Cited

U.S. PATENT DOCUMENTS 4,528,137 7/1985 Takahara et al. ................ 260/397.4
4,678,609 7/1987 Engels ............................. 260/397.4

Primary Examiner—Brian E. Hearn
Assistant Examiner—Andrew Griffis
Attorney, Agent, or Firm—Millen, White & Zelano

[57] ABSTRACT

6α,9α-difluoro-11β,17α-dihydroxy-16α-methyl-4-pregnene-3,20-dione and its derivatives of general formula I

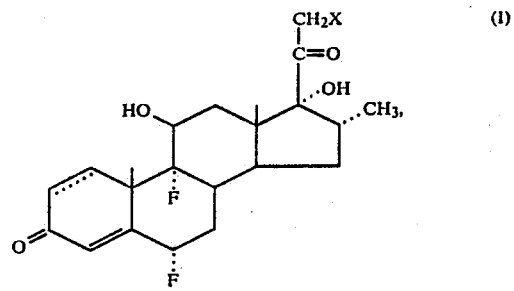

wherein
--- symbolizes a single bond or a double bond, and
X is H, Br, I or alkanoyloxy with 1–8 carbon atoms, are prepared by a novel process from 3β,17α-dihydroxy-16α-methyl-5-pregnen-20-one. The resultant pregnene derivatives are useful as intermediates in the production of flumethasone.

10 Claims, No Drawings

PROCESS FOR PRODUCTION OF 6α,9α-DIFLUORO-11β,17α-DIHYDROXY-16α-METHYL-4-PREGNENE-3,20-DIONE AND ITS DERIVATIVES

BACKGROUND OF THE INVENTION

The invention relates to a process for the production of 6α,9α-difluoro-11β,17α-dihydroxy-16α-methyl-4-pregnene-3,20-dione and its derivatives of general formula

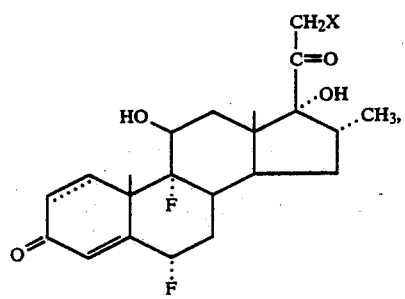

wherein
 ≡≡≡symbolizes a single bond or a double bond and
 X represents a hydrogen atom, a bromine atom, an iodine atom or an alkanoyloxy group with a maximum of 8 carbon Pregnene derivatives of formula I are useful as intermediates for production of the corticoid, flumethasone, i.e., 6α,9α-difluoro-11β,17α, 21-trihydroxy-16α-methyl-1,4-pregnadiene-3,20-dione. Flumethasone is a known corticoid active ingredient. However, synthesis of flumethasone is very expensive (J. A. Edwards et al., J. Amer. Chem. Soc., 82, 1960, 2318–2322).

SUMMARY OF THE INVENTION

It is an object of this invention to provide a process for producing flumethasone and intermediates thereof in a simple manner while attaining significantly higher yields than possible by the previously known syntheses. Upon further study of the specification and appended claims, further objects and advantages of this invention will become apparent to those skilled in the art. These objects are achieved by providing a process for the production of pregnene derivatives of the Formula I

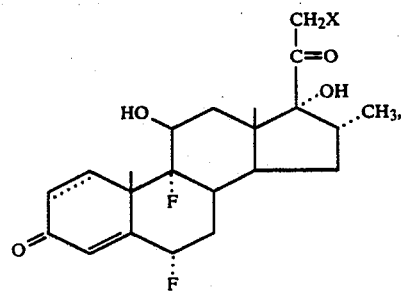

wherein
 ≡≡≡symbolizes a single bond or a double bond, and
 X is H, Br, I or alkanoyloxy of 1–8 carbon atoms,
comprising reacting a 3β,17α-dihydroxy-16α-methyl-5-pregnen-20-one of formula II

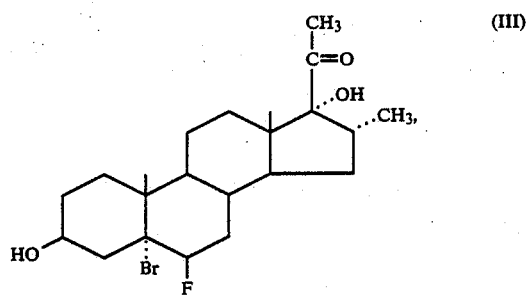

with an N-bromoacylamide and hydrogen fluoride in the presence of urea,
 oxidizing the resultant 5α-bromo-6β-fluoro-3β,17α-dihydroxy-16α-methyl-pregnan-20-one of formula III

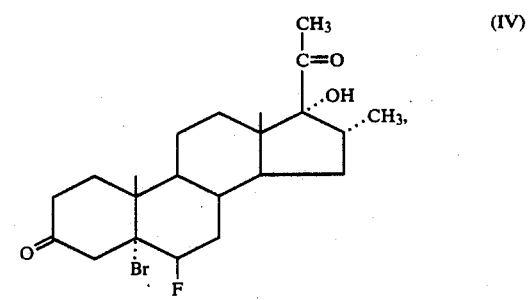

by means of chromic acid,
 splitting off hydrogen bromide (dehydrobrominating) from the formed 5α-bromo-6β-fluoro-17α-hydroxy-16α-methyl-pregnane-3,20-dione of formula IV

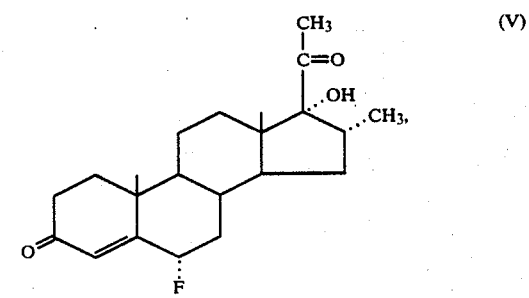

hydroxylating the thus-produced 6α-fluoro-17α-hydroxy-16α-methyl-4-pregnene-3,20-dione of formula V at the 11-position by means of a live culture of Curvularia lunata splitting off water (dehydrating) from the resultant 6α-fluoro-11β,17α-dihydroxy-16α-methyl-4-pregnene-3,20-dione of formula VI

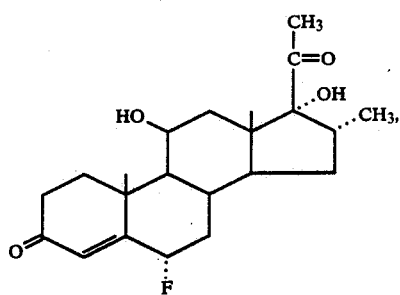
(VI)

adding BrOH to the resultant 6α-fluoro-17α-hydroxy-16α-methyl-4,9,(11)-pregnadiene-3,20-dione of formula VII

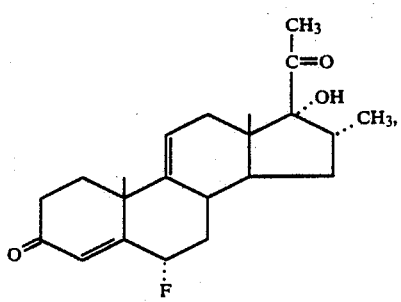
(VII)

splitting off hydrogen bromide from the resultant 9α-bromo-6α-fluoro-11β,17α-dihydroxy-16α-methyl-4-pregnene-3,20-dione of formula VIII

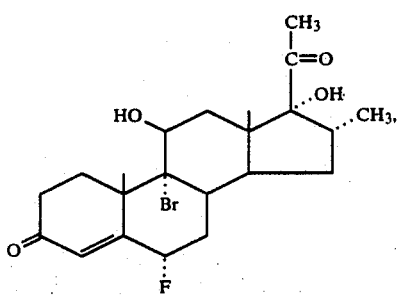
(VIII)

opening the epoxide ring of the resultant 9,11β-epoxy-6α-fluoro-17α-hydroxy-16α-methyl-4-pregnene-3,20-dione of formula IX

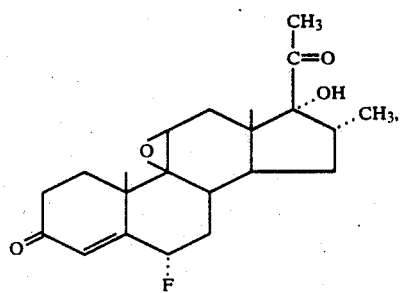
(IX)

by means of hydrogen fluoride to form 6α, 9α-difluoro-11β, 17α-dihydroxy-16α-methyl-4-pregnene-3, 20-dione of formula Ia

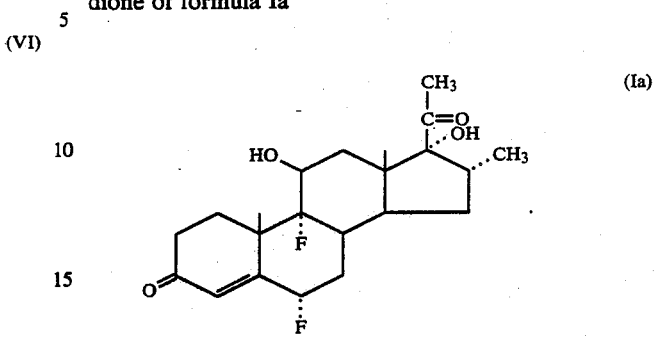
(Ia)

Optionally, the thus-produced pregnene derivative is dehydrogenated by fermentation with microorganisms capable of steroid delta¹ dehydrogenation, to form 6α,-9α-difluoro-11β, 17α-dihydroxy-16α -methyl-1,4-pregnadiene-3,20-dione of formula Ib

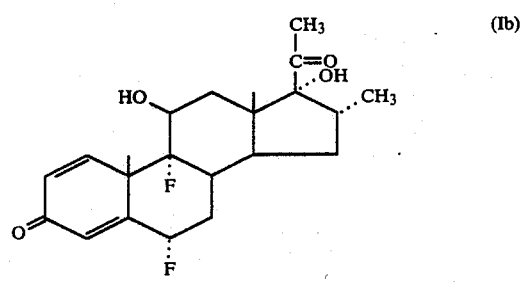
(Ib)

In addition, the formed 1,4-pregnadiene-3,20-dione can, optionally, be halogenated to 6α,9α-difluoro-11β,17α-dihydroxy-21-halogen-16α-methyl-1,4-pregnadiene-3,20-dione of formula Ic

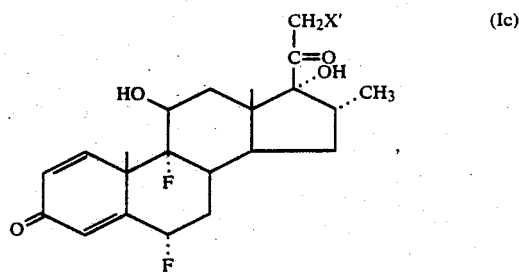
(Ic)

wherein

X represents a bromine atom or iodine atom, by means of bromine or iodine.

Furthermore, the formed 21-halogen-1,4-pregnadiene-3,20-dione can be converted to 21-alkanoyloxy-6α,-9α-difluoro-11β,17α-dihydroxy-16α-methyl-1,4-pregnadiene-3,20-dione of formula Id

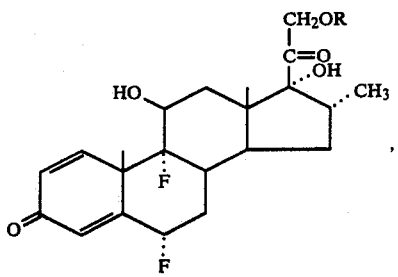

wherein
- R is an alkanoyl group with a maximum of 8 carbon atoms, by exchanging iodine or bromine for an alkanoyloxy group.

In the first step of the process according to the invention, 3β,17α-dihydroxy-16α-methyl-5-pregnen-20-one is reacted with an N-bromoacylamide (for example, N-bromoacetamide or especially N-bromosuccinimide) and hydrogen fluoride. If this reaction is performed under the conditions that are usually used for addition of a bromine or fluorine atom to the 5(6)-double bond of a steroid (J. Fried et al. Organic Reactions in Steroid Chemistry, van Nostrand Reinhold Co., New York et al., Vol.1, 1972, 454ff), only small yields of the process product are obtained. On the other hand, surprisingly high yields of the desired 5α-bromo-6β-fluoro-3β,17α-dihydroxy-16α-methyl-pregnan-20-one are obtained if the reaction is performed in the presence of urea. Favorable conditions for performance of this reaction step, for example, are the following:

3β,17α-dihydroxy-16αmethyl-5-pregnen-20-one is suspended in an inert solvent, mixed with a previously prepared urea-hydrogen fluoride reagent and then, by portions, mixed with N-bromoacylamide, and the reaction temperature is about −20° C. to +10° C. Suitable inert solvents are, for example, aromatic hydrocarbons, such as benzene, toluene, xylene, etc. or chlorinated hydrocarbons such as dichloromethane, trichloromethane or tetrachloroethane, suitable urea-hydrogen fluoride reagents are those which contain about 30 to 70% by weight of hydrogen fluoride. The N-bromo-acylamide can contain 2-8 C-atoms, for example. Typical reaction times are for example 30 min. to 8 hours and, typically, 2-30 moles of HF-urea complex are used per mole of steroid. The starting material is known; see, e.g., J. Org. Chem. 26, 1961, 871–878.

The 5α-bromo-6β-fluoro-3β,17α-dihydroxy-16α-methylpregnan-20-one is oxidized to 5α-bromo-6β-fluoro-17α-hydroxy-16α-pregnane-3,20-dione in a second reaction step by means of chromic acid. This reaction step can be performed under the conditions that conventionally are used in the oxidation of hydroxysteroids to oxosteroids by means of chromic acid (J. Fried et al. Organic Reactions in Steroid Chemistry, van Nostrand Reinhold Co., New York et al., Vol.1, 1972, 227ff). But, especially high yields of the process product are attained if the oxidation is performed by means of chromic acid-sulfuric acid in a polar ether (dioxane, tetrahydrofuran, etc.) as solvent instead of acetone. Other possible oxidations include the Oppenauer oxidation or microbiological oxidation by Flavobacterium dehydrogenans. See C. Djerassi, "Steroid Reactions", Holden Day Inc., S.F. 1983, p. 89ff.

Hydrogen bromide is split out of the resulting 5α-bromo-6β-fluoro-17α-hydroxy-16α-methyl-pregnane-3,20-dione in a way known in the art. It is especially advantageous to perform this dehydrobromination by means of strong acids as catalysts, since under these conditions the 6-fluoroatom is isomerized at the same time. Suitable conditions are, for example, the reaction of the bromine compound by means of hydrogen bromide or hydrogen chloride in polar solvents such as acetic acid. See, e.g., Djerassi, "Steroid Reactions," Holden Day, Inc., S.F. 1983, 179ff and 227.

The 6α-fluoro-17α-hydroxy-16α-methyl-4-pregnene-3,20dione thus obtained is hydroxylated in the 11 position in a way known in the art with a live culture of fungi of the species Curvularia. Fungi of the species Curvularia suitable for hydroxylation are, for example, Curvularia falcata QM-102.H, Curvularia genticulata IFO (6284) and Curvularia lunata NRRL 2380, NRRL 2434 or ATCC 12017. The hydroxylation can be performed under the usual conditions, as, for example, described in European patent No. 0003341 but the yields are surprisingly high since there is no 21-hydroxy group in the starting material, heretofore considered necessary for a high yield.

Water is split out of the thus produced 6α-fluoro-11β,17α-dihydroxy-16α-methyl-4-pregnene-3,20-dione in the next reaction step of the process according to the invention. This dehydratation can be performed under the conditions well-known to a man of the art. Suitable conditions are, for example, the dehydratation by means of thionyl chloride in pyridine, by means of phosphoroxychloride in pyridine, or by means of methanesulfonic acid chloride and sulfur dioxide in dimethylformamide/collidine. The reaction of 6α-fluoro-11β,17α-dihydroxy-16α-methyl-4-pregnene-3,20-dione with N-bromoacylamides (especially N-bromoacetamide) in pyridine and then treatment of the reaction mixture with sulfur dioxide has proven to be a very useful method. The conditions under which these dehydratation processes are performed are conventional (J. Fried et al. Organic Comp. New York et al., Vol.1, 1972, p. 320 ff). The N-bromoacylamide typically has 2-8 C-atoms.

BrOH is added in the usual way to the 6α-fluoro-17α-hydroxy-16α-methyl-4,9,(11)-pregnadiene-3,20-dione thus produced. This can occur, for example, by allowing N-bromoacylamides (N-bromoacetamide or especially N-bromosuccinimide) to act on these compounds in the presence of aqueous solvents (such as aqueous acetone, dioxane or tetrahydrofuran). It is known that this reaction can be performed using acids (hydrochloric acid or perchloric acid) as catalysts. See, e.g., U.S. Pat. Nos. 3,232,839, 3,718,671 and 3,678,034. The N-bromoacylamide typically has 2-8 C-atoms.

The 9α-bromo-6α-fluoro-11β,17α-dihydroxy-16α-methyl-4-pregnene-3,20-dione thus obtained is converted into 9β,11β-epoxy-6α-fluoro-17α-hydroxy-16α-methyl-4-pregnene-3,20-dione by splitting off hydrogen bromide in a way known in the art by means of bases (sodium hydroxide, sodium acetate, i.e.) (J. Fried et al. Organic Reactions in Steroid Chemistry, van Nostrand Reinhold Co., New York et al., Vol. II, 1972, 15 ff).

The epoxide ring of the 9β,11β-epoxy-6α-fluoro-17α-hydroxy-16α-methyl-4-pregnene-3,20-dione is opened by means of hydrogen fluoride, and 6α,9α-difluoro-11β,17 -dihydroxy-16α-methyl-4-pregnene-3,20-dione is obtained. The conditions under which this reaction step is performed are also conventional (J. Fried et al.

Organic Reactions in Steroid Chemistry, van Nostrand Reinhold Co., New York et al., Vol. 1, 1972, 425 ff).

If desired, the resulting 6α,9α-difluoro-11β,17α-dihydroxy-16α-methyl-4-pregnene-3,20-dione can be dehydrogenated to 6α,9α-difluoro-11β,17α-dihydroxy-16α-methyl-1,4-pregnadiene-3,20-dione by means of microorganisms capable of steroid-delta[1] dehydrogenation. Suitable microorganisms for dehydrogenation are, for example, those of the species Bacillus (such as, for example, *Bacillus lentus* ATCC 13805, or *Bacillus sphaericus* ATCC 7054 and ATCC 7055) or the species Arthrobacter (as, for example, *Arthrobacter simplex* ATCC 6945). The conditions under which this reaction step can be performed are conventional and, for example, described in European patent application Nos. 0003341 or 0054810.

The resulting 6α,9α-difluoro-11β,17α-dihydroxy-16α-methyl-1,4-pregnadiene-3,20-dione can be converted into the corresponding 21-iodine derivative in a way known in the art. The Stork process for 21-iodine introduction has proven to be especially advantageous (J. Fried et al. Organic Reactions in Steroid Chemistry, van Nostrand Reinhold Co., New York et al., Vol. II, 1972, 207).

The resulting 21-bromine or 21-iodine compounds, if desired, can be converted into the 21-alkanoyloxy-6α,9α-difluoro-11β,17α-dihydroxy-16α-methyl-1,4-pregnadiene-3,20dione of general formula Id, by reacting them in the presence of bases with suitable acids (J. Fried et al. Organic Reactions in Steroid Chemistry, van Nostrand Reinhold Co., New York et al., Vol. II, 1972, 203–212 and 220–227). Preferably acetic acid is used as the acid, which is allowed to act on the 21-halogen compound in an inert solvent such as acetone in the presence of bases, such as sodium acetate or triethylamine. Suitable acids are $C_{2-8}$-alkane carboxylic acids generally.

Saponification of the 21-acetate to 6α,9α-difluoro-11β,17α,21-trihydroxy-16α-methyl-1,4-pregnadiene-3,20-dione (flumethasone) is previously known. See, e.g., J. Am. Chem. Soc. 81, 1959, 3156ff. The other esters can be analogously saponified to flumethasone.

It was already mentioned that with the help of the process according to the invention it is possible to produce flumethasone in a substantially simpler way while attaining higher yields than is possible by previously known syntheses. Another advantage of the process according to the invention consists in the fact that in the individual process steps the process products are generally obtained in such high purity (this applies especially for the 11β hydroxylation) that expensive purification crystallizations can be avoided, which in such multistep syntheses generally cause considerable yield losses of the process product.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE (a) To a suspension of 180.7 g of 3β,17α-dihydroxy-16α-methyl-5-pregnen-20-one in 1445 ml of toluene is added, in a polyethylene vessel with stirring at 0° C., 240.2 ml of ureahydrofluoric acid reagent (45:55% by weight) and then 97.3 g of N-bromosuccinimide is added in portions so that the temperature is at about 0° to 3° C. The suspension is restirred for 2 hours at 0° C. and then added to a mixture of 2 kg of ice and 1441 ml of 25% ammonia. The toluene is distilled off with steam, the aqueous suspension is cooled to 20° C., the reaction product is suctioned off and rewashed well with about 700 ml of water. The product, wet with water, is absorptively precipitated, first with 813 ml of ethyl acetate and then twice more each time with 500 ml of ethyl acetate, and suctioned off and dried at 30° C. in a circulating air drying cabinet.

Yield: 166 g of 5α-bromo-6β-fluoro-3β,17α-dihydroxy-16α-methyl-pregnan-20-one with a melting point of 183° to 185° C. (decomp.).

(b) To a suspension of 165 g of 5-bromo-6β-fluoro-3β,17-dihydroxy-16-methyl-pregnan-20-one in 1655 ml of tetrahydrofuran and 58 ml of water is added 258 ml of 8N chromic acid solution (produced by dissolving 267.2 g of chromium(VI) oxide in 230 ml of concentrated sulfuric acid and diluting the mixture with water to 1000 ml) so that the temperature is 0° to 2° C. and it is restirred for 2 more hours at this temperature. Then 15 ml of 2-propanol is added to it, it is stirred for another 10 minutes and the reaction product is precipitated in 8.3 liters of ice water, suctioned off and washed three times, each time with 250 ml of water. The water-moist product is vigorously stirred in 414 ml of acetone for 15 minutes at 20° C., suctioned off and washed twice, each time with 50 ml of acetone. A sample of 5α-bromo-6β-fluoro-17α-hydroxy-16α-methyl-pregnane-3,20-dione, carefully dried in a vacuum, has a melting point of 105° to 115° C. (decomp.).

The filter-moist 5α-bromo-6β-fluoro-17α-hydroxy-16α-methyl-pregnane-3,20-dione is suspended in 1655 ml of acetic acid, heated to 30° C. and mixed with 5.36 ml of hydrogen bromide in glacial acetic acid, 33% by weight, with stirring. After about 30 minutes, a clear solution occurs. Then it is stirred for another 30 minutes at 30° C. Then 35.1 g of sodium acetate is added and precipitation is performed in 6.62 liters of ice water. The suspension is stirred for 30 minutes more, the reaction product is suctioned off, washed twice, each time with a solution of 17.5 g of sodium acetate in 250 ml of water and once with 250 ml of water and dried at 30° C. in a circulating air drying cabinet.

Yield: 123 g of 6α-fluoro-17α-hydroxy-16α-methyl-4-pregnene-3,20-dione with a melting point of 168° to 184° C. (decomp.).

According to thin-layer chromatography analysis on silica gel plates in the toluene/isopropanol 15:3 system, three passages, the reaction product contains about 10% of 6β-fluoroisomers.

(d) A 2-liter Erlenmeyer flask with 1 liter of sterile nutrient solution, containing 1% corn steep liquor and 1.25% soybean powder, adjusted to pH 6.2, is inoculated with a rinse of a dry culture of *Curvularia lunata* NRRL 2380 and is shaken at 30° C. for 72 hours at 175 revolutions per minute.

A 50-liter fermenter with 30 liters of a sterile nutrient solution, containing 1% corn steep liquor, 1.25% soybean powder and 4 ml of silicon SH, adjusted to pH 6.5, is inoculated with 1 liter of *Curvularia lunata* growth culture and this initial culture is incubated at 30° C. with aeration with 2 m³ of air per hour at 150 revolutions per minute for 18 hours.

A 50-liter fermenter is charged with 30 liters of a sterile nutrient solution, containing 1% corn steep liquor, 1.25% soybean powder and 4 ml of silicon SH, adjusted to pH 6.5, is inoculated with 3 liters of *Curvularia lunata* initial culture and is incubated at 30° C. with aeration with 2 m³ of air per hour at 150 revolutions per minute for 5 hours.

Then to the culture is added a solution, sterilized by filtration, of 12 g of 6α-fluoro-17α-hydroxy-16α-methyl-4-pregnene-3,20-dione (72.1%) in 600 ml of ethylene glycol monomethyl ether and it is fermented another 35 hours. After addition of the substrate, the aeration is another 2 m³ per hour, the stirring is increased to 220 revolution per minute.

After the fermentation is completed, the culture broth is extracted three times, each time with 20 liters of methyl isobutyl ketone, and the methyl isobutyl ketone extract is evaporated in vacuum in a rotation evaporator at max. 50° C.

After distilling off the total amount of solution, the residue is taken up in 100 ml of ethyl acetate with heating on a steam bath and, after complete dissolution of the residue, is cooled to room temperature.

The crystallizate is suctioned off by a Buechner funnel, rewashed with ethyl acetate and dried at 50° C. in a vacuum drying cabinet.

6.4 g of 6α-fluoro-11β,17α-dihydroxy-16α-methyl-4-pregnene-3,20-dione (96%) is obtained. 1.5 g of this product was detected chromatographically in the mother liquor.

(e) 100 g of 6α-fluoro-11β,17α-dihydroxy-16α-methyl-4-pregnene-3,20-dione is dissolved in 1050 ml of dry pyridine. To the solution is added 39.4 g of N-bromoacetamide at 25° C. and it is restirred for 15 minutes. It is then cooled to 10° C. and sulfur dioxide is introduced at this temperature until the sample runs negative on acidified potassium iodide starch paper. Then 2100 ml of water is instilled at 20° C. It is restirred for 15 hours with cooling with ice water. The precipitate is filtered off, washed neutral with water and dried. 95.5 g of 6α-fluoro-17α-hydroxy-16α-methyl-4,9(11)-pregnadiene-3,20-dione is obtained, which after recrystallization from diisopropyl ether melts at 219° to 225° C.

(f) A solution of 31.7 g of N-bromosuccinimide is instilled with cooling to a suspension of 50 g of 16α-fluoro-17α-hydroxy-16α-methyl-4,9(11)-pregnadiene-3,20-dione raw product in 500 ml of acetone and 100 ml of water. It is restirred for 2 hours. When the reaction is completed, 1.1 liter of water is added to the reaction mixture. The precipitated 9α-bromo-6α-fluoro-11β,17α-dihydroxy-16α-methyl-4-pregnene-3,20-dione is filtered off, washed and suctioned off dry. Melting point of a dry sample: 138° to 143° C. with decomposition. Then the water-moist 9α-bromo-6α-fluoro-11β,17α-dihydroxy-16α-methyl-4-pregnene-3,20-dione is suspended in 400 ml of methanol. 50 g of the sodium carbonate is added to the suspension and restirred at an elevated temperature. It is cooled to room temperature and the 9,11β-epoxy-6α-fluoro-17α-hydroxy-16α-methyl-4-pregnene-3,20-dione is precipitated by addition of water. It is filtered off, washed neutral with water and dried. 41.3 g is obtained with a melting point of 210° to 214° C.

(g) 50 g of 9,11β-epoxy-6α-fluoro-17α-hydroxy-16α-methyl-4-pregnene-3,20-dione is suspended in 175 ml of methylene chloride and is added to 175 ml of ureahydrofluoric acid reagent (45:55% by weight) with cooling. Then it is stirred for 2 more hours at room temperature. After addition of 500 ml of ice water, it is neutralized with conc. ammonia and the methylene chloride is distilled off with steam. The reaction product is suctioned off, washed with water, dried in a circulating drying cabinet at 50° C. and recrystallized from methylene chloride/methanol. 38 g of 6α,9α-difluoro-11β,17α-dihydroxy-16α-methyl-4-pregnene-3,20dione, which melts at 254° to 258° C. with decomposition, is obtained.

(h) A 2-liter Erlenmeyer flask with 1 liter of sterile nutrient solution containing 0.05% glucose, 1.0% of yeast extract, 0.5% of corn steep liquor, adjusted to pH 7.0, is inoculated with a rinse of *Bacillus lentus* ATCC 13805 and shaken at 30° C. for 48 hours with 180 revolutions per minute.

A 50-liter fermenter with 30 liters of sterile nutrient solution containing 0.05% glucose, 1.0% of yeast extract, 0.5% of corn steep liquor and 4 ml of silicon SH, adjusted to pH 7.0, is inoculated with one liter of *Bacillus lentus* growth culture. This initial culture is incubated at 30° C. with aeration of 2 m³ of air per hour and stirring at 220 revolutions per minute for 24 hours.

A 50-liter fermenter is charged with 30 liters of sterile nutrient solution containing 0.05% glucose, 1.0% of yeast extract, 0.5% of corn steep liquor and 4 ml of silicon SH, adjusted to pH 7.0, is inoculated with 3 liters of *Bacillus lentus* initial culture and is incubated at 30° C. with aeration of 2 m³ of air per hour and stirring at 300 revolutions per minute for 6 hours.

3 g of 6α,9α-difluoro-11β,17α-dihydroxy-16α-methyl-4-pregnene-3,20-dione in 300 ml of 2-methoxyethanol is added and it is fermented another 12 hours.

After the fermentation is completed, the culture broth, sterilized with 1% formalin, is extracted three times, each time with 20 liters of methyl isobutyl ketone, and the methyl isobutyl ketone extract is evaporated in a vacuum in a rotation evaporator at max. 50° C.

After distilling off the total amount of solution, the residue is taken up in 100 ml of ethyl acetate with heating on a steam bath and, after complete dissolution of the residue, is cooled to room temperature.

The crystallizate is suctioned off by a Buechner funnel, rewashed with ethyl acetate and dried at 50° C. in a vacuum drying cabinet.

2.6 g of 6α,9α-difluoro-11β,17α-dihydroxy-16α-methyl-1,4-pregnadiene-3,20-dione is obtained.

(i) To a suspension of 10 g of 6α,9α-difluoro-11β,17α-dihydroxy-16α-methyl-1,4-pregnadiene-3,20-dione in 80 ml of methanol is added 10 ml of a saturated methanolic calcium chloride solution and 5.4 g of calcium oxide under nitrogen at 25° C. with stirring. To this is added within 1.5 hours a solution of 21.6 g of iodine and 3.2 g of calcium chloride in 62 ml methanol and it is restirred three hours at 25° C. It is precipitated in 300 ml of ice water, 30 ml of 10% acetic acid is added and then 15 ml of 10% sodium thiosulfate solution is added and stirred for 15 more minutes. The reaction product is suctioned off and washed well with water.

The water-moist 6α,9α-difluoro-11β,17α-dihydroxy-21-iodine-16α-methyl-1,4-pregnadiene-3,20-dione is suspended in 110 ml of acetone. 16.7 ml of acetic acid and 27.1 ml of triethylamine is added to the reaction mixture and it is stirred for 3.5 hours at 50° C. The solution is evaporated in a vacuum to about 75 ml and precipitated in 500 ml of ice water. The suspension is restirred for one hour, the reaction product is suctioned off, washed several times with water and dried at 50° C. in a circulating air drying cabinet. 11.2 g of 21-acetoxy-6α,9α-difluoro-11β,17α-dihydroxy-16α-methyl-1,4-pregnadiene-3,20-dione with a melting point of 260° to 264° C. (from acetone/diisopropyl ether) is obtained in this way.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 6α,9α-difluoro-11β,17α-dihydroxy-16α-methyl-4-pregnene-3,20-diones of general formula I

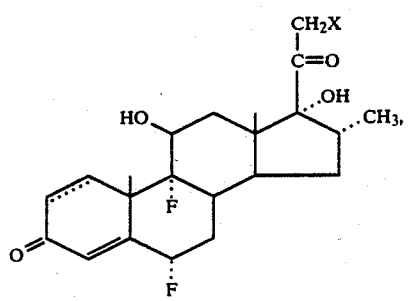

wherein

═══symbolizes a single bond or a double bond, and

X is H, Br, I or alkanoyloxy with 1-8 carbon atoms, comprising: reacting 3β,17α-dihydroxy-16α-methyl-5-pregnen-20-one of formula II

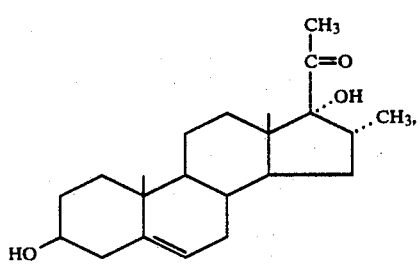

with an N-bromoacylamide and hydrogen fluoride in the presence of urea, oxidizing the resultant 5α-bromo-6β-fluoro-3β,17α-dihydroxy-16α-methyl-pregnan-20-one of formula III

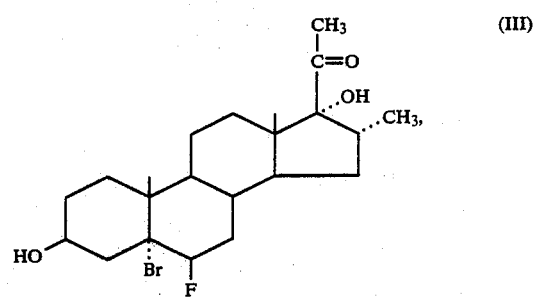

dehydrobrominating the formed 5α-bromo-6β-fluoro-17β-hydroxy-16α-methyl-pregnane-3,20-dione of formula IV while simultaneously isomerizing the 6-position

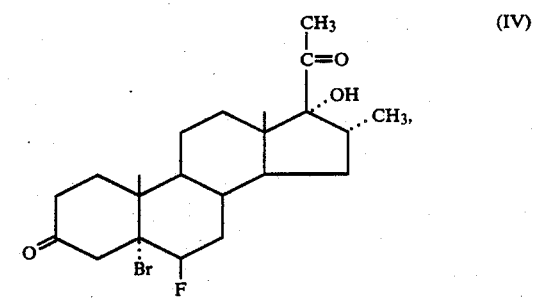

hydroxylating the resultant 6α-fluoro-17α-hydroxy-16α-methyl-4-pregnane-3,20-dione of formula V at the 11-position

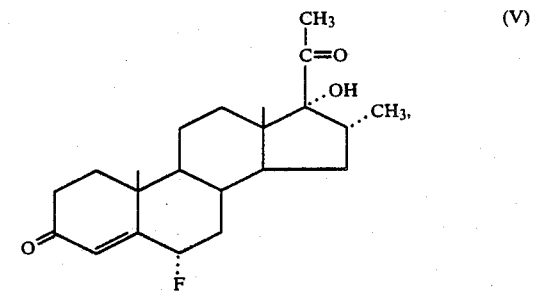

with a live culture of an effective species of the Curvularia type, dehydrating the thus-produced 6α-fluoro-11β,17α-dihydroxy-16α-methyl-4-pregnene-3,20-dione of formula VI

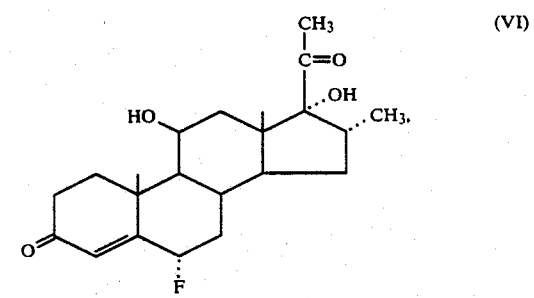

adding BrOH to the resultant 6α-fluoro-17α-hydroxy-16α-methyl-4,9,(11)-pregnadiene-3,20-dione of formula VII

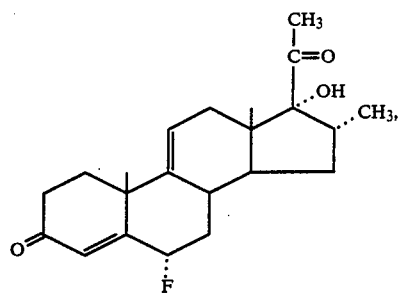

(VII)

dehydrobrominating the resultant 9α-bromo-6α-fluoro-11β,17α-dihydroxy-16α-methyl-4-pregnene-3,20-dione of formula VIII

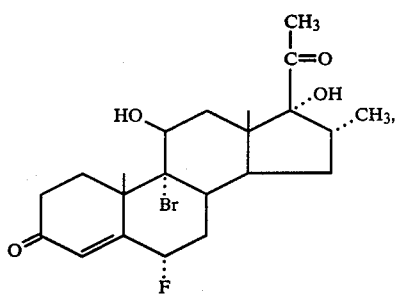

(VIII)

and opening the epoxide ring of the thus-produced 9,11β-epoxy-6α-fluoro-17α-hydroxy-16α-methyl-4-pregnene-3,20-dione of formula IX

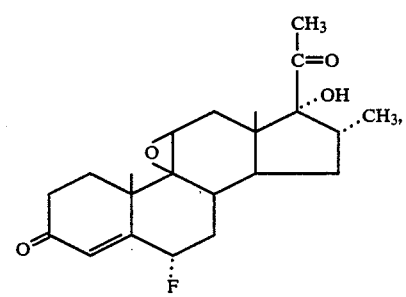

(IX)

with hydrogen fluoride to form 6α,9α-difluoro-11β,17α-dihydroxy-16α-methyl-4-pregnene-3,20-dione of formula Ia

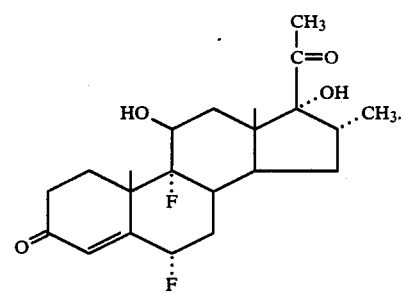

(Ia)

2. A process according to claim 1, further comprising dehydrogenating the 6α,9α-difluoro-11β,17α-dihydroxy-16α-methyl-4-pregnene-3,20-dione of formula Ia by fermentation, with microorganisms capable of steroid delta¹ dehydrogenation, to produce the 6α,9α-difluoro-11β,17α-dihydroxy-16α-methyl-1,4-pregnadiene-3,20-dione of formula Ib

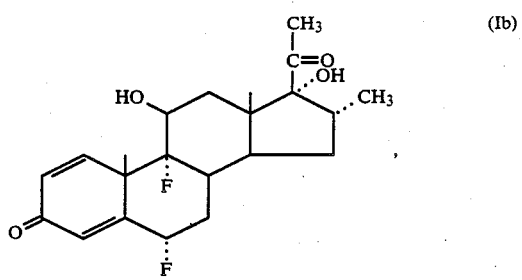

(Ib)

3. A process according to claim 2, further comprising brominating or iodinating 6α,9α-difluoro-11β,17α-dihydroxy-16α-methhyl-1,4-pregnadiene-3,20-dione of formula Ib in the 21-position to produce 6α,9α-difluoro-11β,17α-dihydroxy-21-halogen-16α-methyl-1,4-pregnadiene-3,20-dione of formula Ic

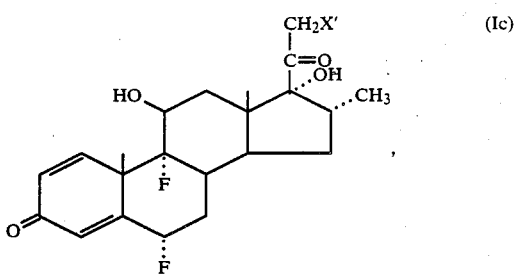

(Ic)

wherein

X' is Br or I.

4. A process according to claim 3, further comprising reacting an acid, R¹COOH, wherein R¹ is $C_{1-7}$-alkyl, with 6α,9α-difluoro-11β,17α-dihydroxy-21-halogen-16α-methyl-1,4-pregnadiene-3,20-dione of Formula Ic, in the presence of a base, to produce 21-alkanoyloxy-6α,9α-difluoro-11β,17α-dihydroxy-16α-methyl-1,4-pregnadiene-3,20-dione of formula Id

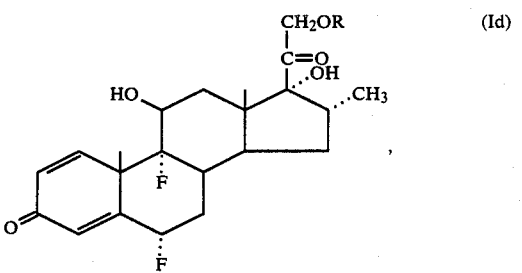

(Id)

wherein

R represents an alkanoyl group having 1–8 carbon atoms.

5. A process for the production of 6α,9α-difluoro-11α,17α,21-trihydroxy-16α-methyl-1,4-pregnadiene-3,20-dione comprising preparing a 21-alkanoyloxy-6α,9?α-difluoro-11α,17α-dihydroxy-16α-methyl-1,4-pregnadiene-3,20-dione compound by the process of claim 4 and saponifying said compound at the 21-position.

6. 5α-Bromo-6β-fluoro-17α-hydroxy-16α-methylpregnane-3,20-dione.

7. 6α-fluoro-17α-hydroxy-16α-methyl-4,9(11)-pregnadiene-3,20-dione.

8. 9α-Bromo-6α-fluoro-11β,17α-dihydroxy-16α-methyl-4-pregnene-3,20-dione.

9. 6α-Fluoro-9,11β-epoxy-17α-hydroxy-16α-methyl-4-pregnene-3,20-dione.

10. A process for preparing an intermediate compound for use in the production of flumethasone comprising reacting 3β,17α-dihydroxy-16α-methyl-5-pregnen-20-one of formula II

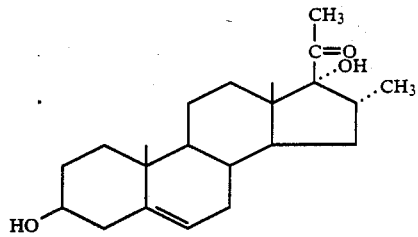

with an N-bromoacylamide and hydrogen fluoride in the presence of urea.

* * * * *